United States Patent
Kamath

(10) Patent No.: US 9,469,437 B2
(45) Date of Patent: Oct. 18, 2016

(54) RADIOFREQUENCY SHIELDED CONTAINER

(71) Applicant: CYBERONICS, INC., Houston, TX (US)

(72) Inventor: Anubhav H. Kamath, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 531 days.

(21) Appl. No.: 13/744,801

(22) Filed: Jan. 18, 2013

(65) Prior Publication Data
US 2014/0202905 A1 Jul. 24, 2014

(51) Int. Cl.
*A61B 19/02* (2006.01)
*A61N 1/04* (2006.01)
*B65D 25/14* (2006.01)
*A61N 1/372* (2006.01)

(52) U.S. Cl.
CPC ........... *B65D 25/14* (2013.01); *A61N 1/37211* (2013.01); *A61N 2001/37294* (2013.01)

(58) Field of Classification Search
CPC .................. B65D 25/14; A61N 2001/37294; A61N 1/37211
USPC .................. 206/438, 484, 484.2, 524.1, 525, 206/570–572; 607/1, 36, 60
See application file for complete search history.

(56) References Cited

U.S. PATENT DOCUMENTS

| | | |
|---|---|---|
| 3,508,538 A | 4/1970 | Keller, Jr. |
| 3,625,201 A | 12/1971 | Murphy, Jr |
| 3,800,801 A | 4/1974 | Gaillard |
| 4,347,849 A | 9/1982 | Congdon |
| 4,423,732 A | 1/1984 | Tarjan et al. |
| 4,476,869 A | 10/1984 | Bihn |
| 4,556,061 A | 12/1985 | Barreras et al. |
| 4,585,004 A | 4/1986 | Brownlee |
| 4,605,007 A | 8/1986 | Heraly |
| 4,705,042 A | 11/1987 | Giurtino |
| 4,830,005 A | 5/1989 | Woskow |
| 4,979,506 A | 12/1990 | Silvian |
| 5,003,975 A | 4/1991 | Hafelfinger et al. |
| 5,237,991 A | 8/1993 | Kamm |
| 5,456,698 A * | 10/1995 | Byland et al. .................. 607/36 |
| 5,470,345 A * | 11/1995 | Hassler et al. .................. 607/36 |
| 6,154,675 A | 11/2000 | Juran et al. |
| 7,020,525 B1 * | 3/2006 | Davis et al. .................... 607/36 |
| 7,308,316 B2 * | 12/2007 | Schommer ...................... 607/61 |

(Continued)

OTHER PUBLICATIONS

Center et al, "Measurement of cardiac stimulation threshold by transcutaneous needle puncture", Journal of Thoracic & Cardiovascular Surgery, V. 61, No. 5, May 1971, pp. 752-754.

*Primary Examiner* — Luan K Bui
(74) *Attorney, Agent, or Firm* — Foley & Lardner LLP

(57) ABSTRACT

A system includes a first sterile medical device container. The first sterile medical device container is transparent to radiofrequency (RF) signals in a particular frequency range. The system also includes a sterile medical device within the first sterile medical device container. The sterile medical device is capable of radiofrequency communication through the first sterile medical device container using the particular frequency range. The system further includes a second container fully enclosing the first sterile medical device container and the sterile medical device, the second container including RF shielding material that is substantially opaque to the RF signals in the particular frequency range.

17 Claims, 3 Drawing Sheets

(56) References Cited

U.S. PATENT DOCUMENTS

| | | | |
|---|---|---|---|
| 7,596,850 B2 * | 10/2009 | Barth | B65D 31/02 257/704 |
| 7,769,457 B2 * | 8/2010 | Fonte | 607/36 |
| 7,957,813 B1 | 6/2011 | Persson et al. | |
| 8,059,628 B2 | 11/2011 | Bradley et al. | |
| 8,128,953 B2 | 3/2012 | Yang et al. | |
| 8,170,515 B2 | 5/2012 | Le Reverend et al. | |
| 2008/0048836 A1 | 2/2008 | Bungartz et al. | |
| 2008/0132922 A1 | 6/2008 | Buevich et al. | |
| 2012/0055824 A1 * | 3/2012 | Nash | H05K 9/0047 206/320 |
| 2012/0203317 A1 * | 8/2012 | Valentine et al. | 607/116 |
| 2013/0118935 A1 * | 5/2013 | Zar | 206/320 |
| 2014/0190841 A1 * | 7/2014 | Nash | 206/37 |

\* cited by examiner

RADIOFREQUENCY SHIELDED CONTAINER

FIELD OF THE DISCLOSURE

The present disclosure is generally related to shielding implantable medical devices from radiofrequency signals.

BACKGROUND

A control device may communicate with one or more implantable medical devices (IMDs) via a wireless network. When the control device is communicating with a particular IMD, other IMDs may receive and respond to a communication transmitted from the control device even though the other IMDs are not the intended recipients. When an IMD responds to an unintended communication, power is consumed, thus reducing the available power (e.g., battery life) of the IMD to perform other tasks.

SUMMARY

Responding to unintended communications may reduce available power of an implantable medical device (IMD). The systems and methods described herein may advantageously enable an IMD to respond to intended communications, but not unintended communications. For example, an IMD may be stored in a first sterile medical device container that is transparent to radiofrequency (RF) signals in a particular frequency range. The IMD and the first sterile medical device container may be stored in a second container that is opaque to the RF signals in the particular frequency range. The second container may shield the IMD from receiving and responding to the RF signals via a conductive material as the RF signals are intended for another IMD.

A particular embodiment of the disclosure relates to a system which includes a first sterile medical device container. The first sterile medical device container is transparent to RF signals in a particular frequency range. The system also includes a sterile medical device within the first sterile medical device container. The sterile medical device is capable of radiofrequency communication through the first sterile medical device container using the particular frequency range. The system further includes a second container fully enclosing the first sterile medical device container and the sterile medical device. The second container includes RF shielding material that is substantially opaque to the RF signals in the particular frequency range.

Another particular embodiment of the disclosure relates to a method that includes inserting a first sterile medical device container containing a sterile medical device into a second container. The first sterile medical device container is transparent to RF signals in a particular frequency range. The method also includes closing the second container such that the closed second container fully encloses the first sterile medical device container and the sterile medical device to shield the sterile medical device from an interrogation RF signal, transmitted from an interrogator in the particular frequency range, via RF shielding material affixed to the second container. The RF shield material is substantially opaque to the RF signals in the particular frequency range Another particular embodiment of the disclosure relates to a system that includes a first sterile medical device container. The first sterile medical device container is transparent to RF signals in a particular frequency range. The system also includes a sterile medical device within the first sterile medical device container. The sterile medical device is capable of radiofrequency communication through the first sterile medical device container using the particular frequency range. The system further includes a second container fully enclosing the first sterile medical device container and the sterile medical device. The second container is configured to block RF signals in the particular frequency range from being received at the first sterile medical device via RF shielding material.

BRIEF DESCRIPTION OF THE DRAWINGS

The disclosure will become more fully understood from the following detailed description, taken in conjunction with the accompanying drawings.

DETAILED DESCRIPTION

Figure 1:
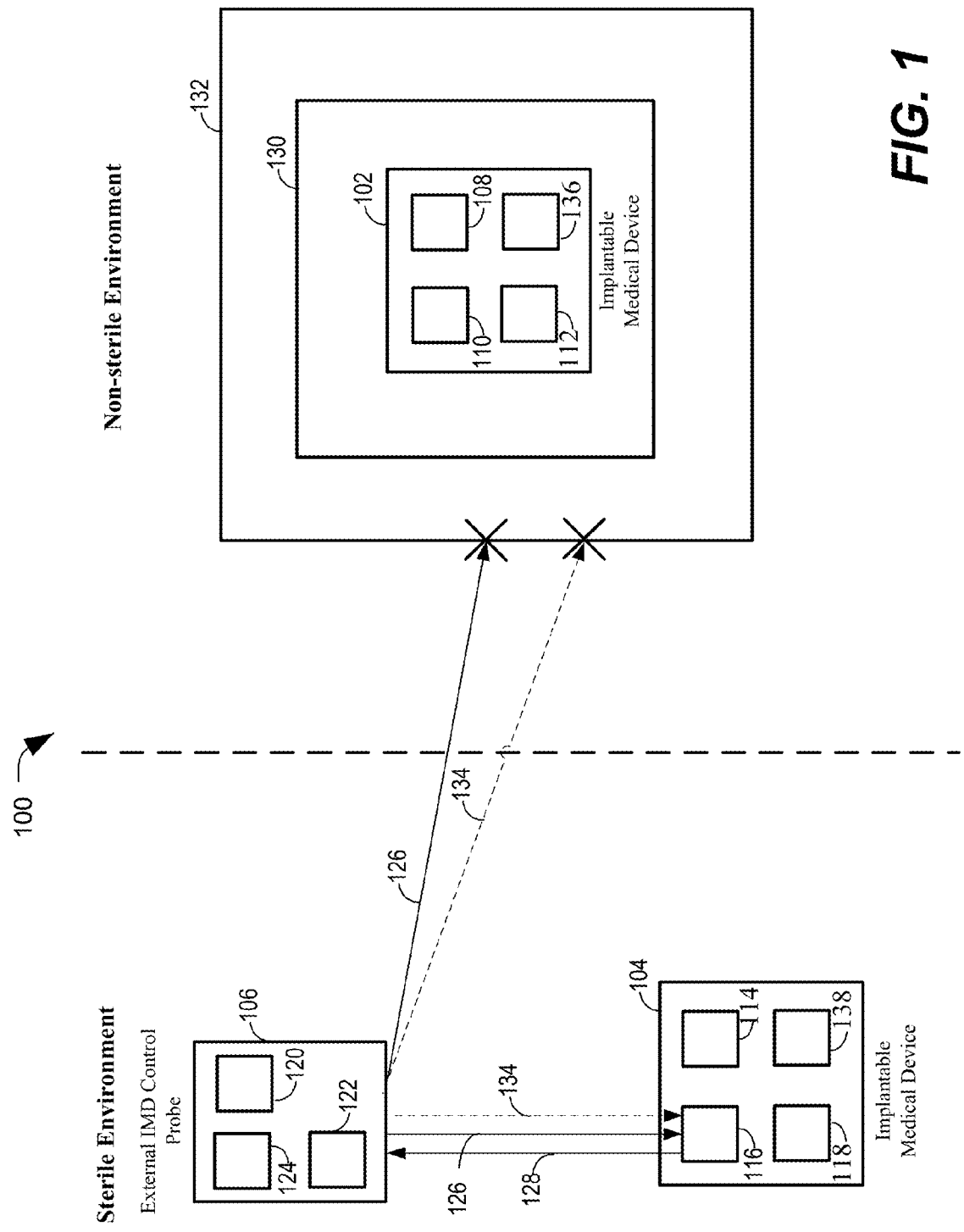
FIG. 1 illustrates a system operable to shield an implantable medical device from RF signals in a particular frequency range according to an exemplary embodiment.

Referring to FIG. 1, a system 100 operable to shield an implantable medical device (IMD) 102 from radiofrequency (RF) signals in a particular frequency is shown according to an exemplary embodiment. The system 100 may include the IMD 102, a second IMD 104, and an external IMD control probe 106.

The IMD 102 may include a wake-up circuit 108, a communication circuit 110, a medical circuitry 112 (e.g., therapy circuitry, sensing circuitry, or a combination thereof), and a power supply 136 (e.g., a battery). The IMD 102 may also include other components (e.g., a processor, a memory, etc.) that are configured to perform different functions. The wake-up circuit 108 may be coupled to the communication circuit 110 and may be configured to, in response to a wake-up signal (e.g., a RF signal in a particular frequency range) received at the wake-up circuit 108, cause the communication circuit 110 to transition from a sleep state in which the communication circuit 110 is inactive to an awake state in which the communication circuit 110 is active (e.g., powered on). The sleep state may be a low power state (e.g., components of the IMD 102 may operate in a standby mode or be turned off to conserve energy). In a particular embodiment, the wake-up circuit 108 may awake another or a different component (e.g., the medical circuit 112) of the IMD 102 in response to the wake-up signal.

The communication circuit 110 may be configured to send signals (e.g., RF signals in the particular frequency range or in a second frequency range) to a device external to the IMD 102, such as the external IMD control probe 106, to receive signals from the device external to the IMD 102, or to both send and receive signals. In a particular embodiment, the communication circuit 110 includes a communication device (e.g., a transceiver). The signals may include data gathered by the medical circuit 112, data related to a condition of the IMD 102 (e.g., a charge state of the power supply 136, a case temperature of the IMD 102, or functionality of a component of the IMD 102, etc.), data related to therapy provided to a patient, program data (e.g., therapy parameters for therapy to be delivered to the patient), etc. The medical circuit 112 may be configured to gather body parameter data from the patient (e.g., heart rate, blood pressure, etc.), determine a medical condition of the patient based on the body parameter data, provide therapy to the patient, or any combination thereof In a particular embodiment, the IMD 102 is an implantable sterile medical device. For example, the IMD 102 may be an implantable neural stimulation device. Examples of the implantable neural stimulation device may include an implantable vagus nerve stimulation device, an implantable spinal cord stimulation device, etc. In another particular embodiment, the IMD 102 is an implantable drug pump. In another particular embodiment, the IMD 102 is an implantable sensor. Examples of an implantable sensor may include an electrocardiogram (ECG) sensor, an electromyogram (EEG) sensor, etc.

The second IMD 104 may be substantially similar to the IMD 102. The second IMD 104 may include a second wake-up circuit 114, a second communication circuit 116, a second medical circuitry 118, and a second power supply 138. The second wake-up circuit 114, the second communication circuit 116, the second medical circuitry 118, and the second power supply 138 may be substantially similar to the wake-up circuit 108, the communication circuit 110, the medical circuit 112, and the power supply 136 respectively. In a particular embodiment, the second wake-up circuit 114 responds to the wake-up signal to transition the second IMD 104 from the sleep state to the awake state.

The external IMD control probe 106 may include a third communication circuit 120, a display 122, and a processing circuit 124. The external IMD control probe 106 may be configured to send signals generated by the processing circuit 124 and/or to receive signals from IMDs via the third communication circuit 120. The external IMD control probe 106 may also be configured to display data at the display 122. For example, the display 122 may display data related to a condition of the external IMD control probe 106. The display 122 may also display data related to a condition of an IMD based on signals received from the IMDs. The display 122 may further display functionality of a component of the external IMD control probe 106. In a particular embodiment, the external IMD control probe 106 is a RF signal interrogator (e.g., a device configured to program IMDs or receive data from the IMDs via RF signals). The external IMD control probe 106 may broadcast RF signals in the particular frequency range to communicate with the second IMD 104. However, the IMD 102 may receive and respond to the RF signals when the IMD 102 is within receiving range of the RF signals, even though the RF signals are not directed to the IMD 102. To prevent reception of the RF signals by the IMD 102, the IMD 102 may be shielded by a container so that the RF signals do not reach the IMD 102. The container is to be described in more detail with reference to FIG. 2.

In the embodiment illustrated in FIG. 1, the external IMD control probe 106 and the second IMD 104 are situated in a sterile environment (e.g., in an operating room). For example, the second IMD 104 may be prepared for use during an operation to implant the second IMD 104 into a patient. The IMD 102 may be stored in a non-sterile environment (e.g., in a warehouse, in a storage room near the operating room) and is not to be used for the operation (i.e., is not prepared for immediate use). During use, before the second IMD 104 is to be implanted into the patient, a user of the external IMD control probe 106 (e.g., a surgeon, a nurse, an assistant, etc.) may use the external IMD control probe 106 to wake up the second IMD 104. For example, the user may wake up the second IMD 104 via the external IMD control probe 106 to initialize the second IMD 104, to check statuses of the second IMD 104, to check functionalities of the second IMD 104, to charge the second IMD 104, to program the second IMD 104, or a combination thereof. To wake up the second IMD 104, the user may use the external IMD control probe 106 to broadcast a first wake-up signal 126 in a particular frequency and/or frequency range. In a particular embodiment, the first wake-up signal 126 is broadcasted at a frequency of approximately 2.45 Gigahertz (GHz).

In a particular embodiment, the first wake-up signal 126 is a RF interrogation signal (e.g., a signal requesting the second IMD 104 to respond with relevant data, such as a device identification of the second IMD 104). In response to receiving the first wake-up signal 126, the second IMD 104 may transition from the sleep state to the awake state and transmit relevant data 128 (e.g., device identification data of the second IMD 104, operational data of the second IMD 104, etc.) back to the external IMD control probe 106. The external IMD control probe 106 may display the relevant data 128 on the display 122.

Because the first wake-up signal 126 is broadcasted, other IMDs (e.g., the IMD 102) within receiving range of the first wake-up signal 126 may also transition to the awake state and respond with corresponding relevant data. In this circumstance, in addition to displaying the relevant data 128, the external IMD control probe 106 may display the other corresponding relevant data received from the other IMDs via the display 122. Thus, the user may have to sort through responses from several IMDs to identify the relevant data 128 for the second IMD 104 to determine whether the second IMD 104 is functioning properly. Furthermore, the IMD 102 responding to the first wake-up signal 126 may waste power as transitioning to the awake state consumes power.

In a particular embodiment, IMDs that are not prepared for implantation, such as the IMD 102, are stored in the non-sterile environment in a manner that prevents IMDs from receiving the first wake-up signal 126. For example, the IMD 102 may be inserted into and stored in a first sterile medical device container 130. The first sterile medical device container 130 may fully enclose the IMD 102. The first sterile medical device container 130 may be transparent to RF signals (e.g., the first wake-up signal 126) transmitted in the particular frequency and/or frequency range. Thus, the IMD 102 may be capable of RF communication through the first sterile medical device container 130 using the particular frequency and/or frequency range while the IMD 102 is stored in the first sterile medical device container 130. The first sterile medical device container 130 may be configured to shield the IMD 102 from contaminants (e.g., dust, germs, etc.) in the non-sterile environment. The first sterile medical device container 130 may be made from plastic or other material that is transparent to the RF signals in the particular frequency and/or frequency range. The first sterile medical device container 130 may have multiple layers and/or compartments to separate one or more tools, accessories, parts (e.g., a torque wrench, wire leads to be used during the implant procedure) from the IMD 102.

The IMD 102 (while stored in the first sterile medical device container 130) may be inserted into and stored (e.g., fully enclosed) in a second container 132 that may be substantially opaque to the RF signals (e.g., the first wake-up signal 126) transmitted in the particular frequency and/or frequency range. When the external IMD control probe 106 broadcasts the first wake-up signal 126, the second container 132 may block the first wake-up signal 126 from reaching the IMD 102. Thus, the IMD 102 does not waste power by transitioning to the awake state in response to the first wake-up signal 126 which is not directed to the IMD 102.

Although FIG. 1 illustrates the IMD 102 in a non-sterile environment and the second IMD 104 in a sterile environment, in another particular embodiment, the IMD 102, the second IMD 104, and the external IMD control probe 106 are situated in a non-sterile environment (e.g., in a factory of an IMD manufacturer or distributor). In this embodiment, the IMD 102 may be tested for defects and placed in the sleep state for storage. The IMD 102 may be stored in the first sterile medical device container 130. The first sterile medical device container 130 with the IMD 102 may be stored (e.g., fully enclosed) in the second container 132. A user (e.g., a factory worker) may use the external IMD control probe 106 to test the functionality of the second IMD 104 before packaging the second IMD 104 for shipment. The user may use the external IMD control probe 106 to broadcast the first wake-up signal 126. In response to receiving the first wake-up signal 126, the second IMD 104 may power on and transmit the corresponding relevant data to the external IMD control probe 106. The user may determine from the corresponding relevant data that the second IMD 104 is functional and broadcast a sleep signal 134 to transition the second IMD 104 to the sleep state. In some embodiments, the second IMD 104 may automatically transition to the sleep state if there is no activity for a predetermined period of time.

The system 100 may thus enable an IMD (e.g., the IMD 102) to save power by blocking RF signals not directed to the IMD from reaching the IMD, thereby preventing the IMD from waking up unintentionally. The system 100 may also enable low cost storage of a sterile IMD that is not in use (e.g., by situating the sterile IMD in a non-sterile environment). The system 100 may further enable a surgeon or a worker to perform functionality check of the IMD in a more efficient manner (e.g., by not displaying data from IMDs that are not intended recipients of the RF signals).

The second container 132 may block the first wake-up signal 126 and the sleep signal 134. Thus, the second container 132 may shield the IMD 102 from receiving the first wake-up signal 126 and the sleep signal 134, and the IMD 102 may remain in the sleep state. The second container 132 may block the first wake-up signal 126 and/or the sleep signal 134 via RF shield material, which is to be described in more detail with reference to FIG. 2.

Figure 2:
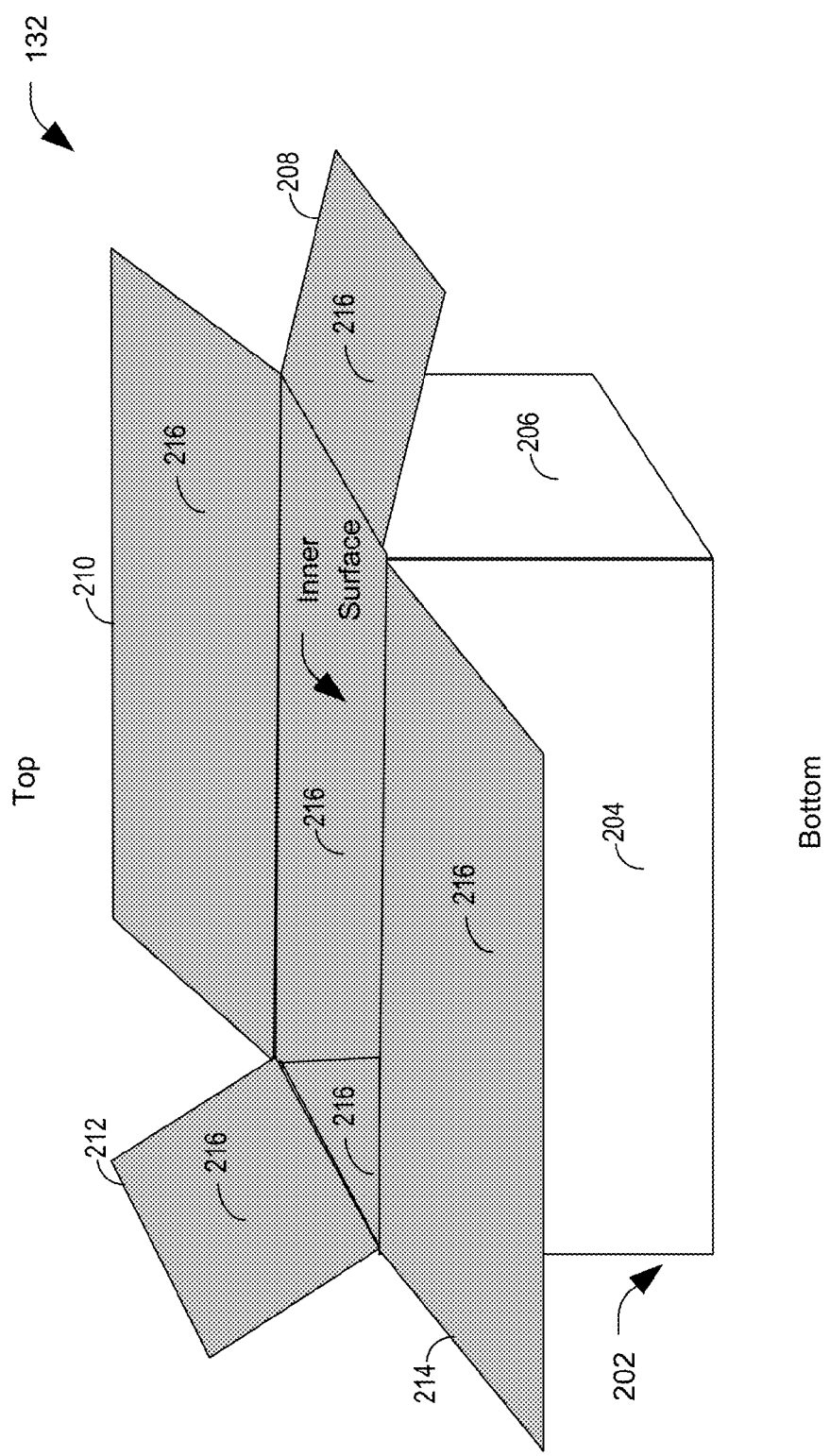
FIG. 2 is an isometric view diagram illustrating a container operable to shield the implantable medical device from the RF signals in the particular frequency range according to an exemplary embodiment.

Referring to FIG. 2, an isometric view diagram 200 illustrating the second container 132 is shown according to an exemplary embodiment. The second container 132 may include a body 202 having multiple sides. In a particular embodiment, the body 202 has four sides (e.g., vertical faces in FIG. 2). For brevity of discussion, only two sides 204 and 206 are shown in FIG. 2. Each side of the body 202 may have a corresponding side flap 208, 210, 212, and 214 on a top edge (e.g., a horizontal face in FIG. 2) of the second container 132 and a corresponding side flap on a bottom edge (e.g., a horizontal face that is not visible in FIG. 2) of the second container 132. For brevity of discussion, only the side flaps 208-214 are shown. After the IMD 102, stored in the first sterile medical device container 130, is inserted into the second container 132, each side flap may be folded over (e.g., towards an inside surface of the second container 132) to fully enclose the IMD 102 and the first sterile medical device container 130 and to shield the IMD 102 from the RF signals (e.g., the first wake-up signal 126, the sleep signal 134). In a particular embodiment, the second container 132 is made from a plant based material (e.g., cardboard). In another particular embodiment, the second container 132 is made from polymer material (e.g., plastic). Although the description of the second container 132 contains many specificities, these specificities are utilized to illustrate some of the exemplary embodiments and should not be construed as limiting. The second container 132 may include any container configuration. For example, instead of flaps the second container 132 may use a lid, may be molded to more or less conform to the shape of the first sterile medical device container 130, may use one or more interlocking parts or mechanisms to enclose the first sterile medical device container 130, may be a bag or sack that the first sterile medical device container 130 is inserted into, or a combination thereof.

When an IMD is fully enclosed by the second container 132, the second container 132 may shield the IMD from RF signals transmitted at the particular frequency and/or frequency range. For example, RF shielding material 216 may block frequency propagation of the RF signals. Thus, the IMD may receive the RF signals when not fully enclosed by the second container 132 (e.g., when a flap of the second container 132 is folded away from the second container 132) and may not receive the RF signals when fully enclosed by the second container 132.

In a particular embodiment, the RF shielding material 216 is affixed to an inner surface of the second container 132 and to a corresponding inner surface of each corresponding flap by adhesive, by spray coating, or by other mechanisms. In a particular embodiment, the RF shielding material 216 is affixed to an outer surface of the second container 132. The RF shielding material 216 may include an electrically conductive material. For example, the RF shielding material 216 may be a metallic foil or a metallic mesh. In a particular embodiment, the second container 132 may include multiple non-conductive layers, and the RF shielding material 216 may be placed between two non-conductive layers. Further, two or more layers of the RF shielding material 216 may be used and separated by one or more non-conductive layers.

Figure 3:
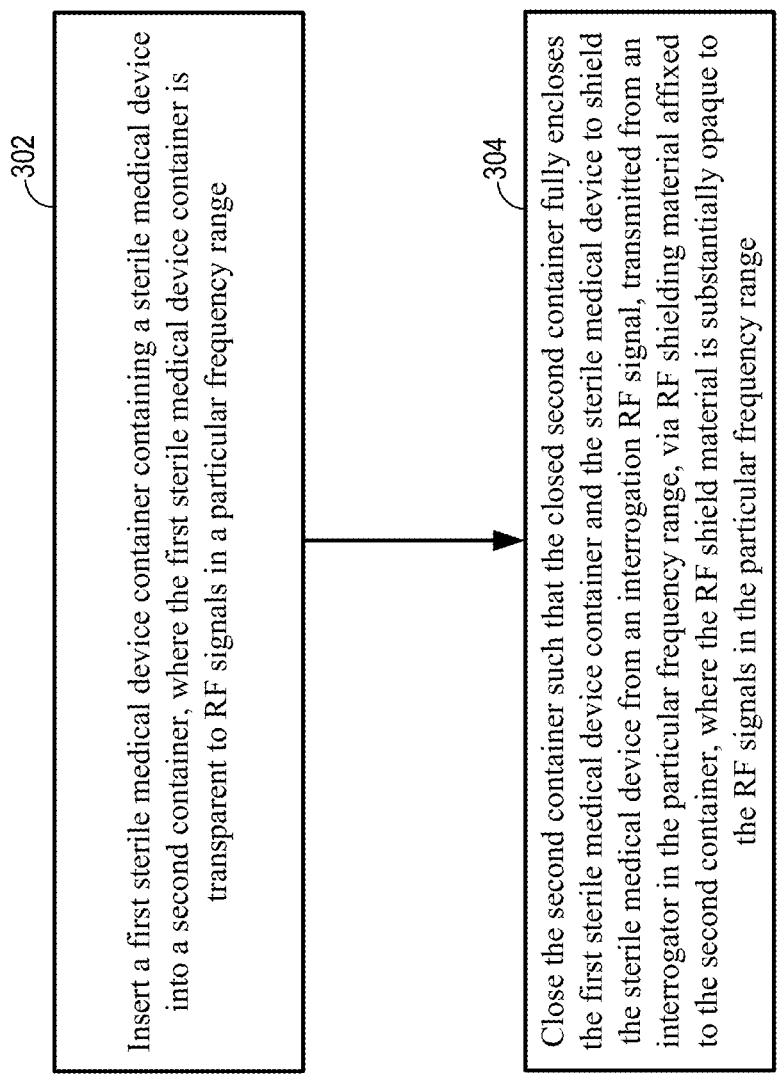
FIG. 3 a flow chart illustrating a method of shielding the implantable medical device from the RF signals in the particular frequency range according to an exemplary embodiment.

Referring to FIG. 3, a process flow chart for a method 300 of shielding the IMD 102 from the RF signals in the particular frequency range according to an exemplary embodiment is shown. The method 300 may include inserting a first sterile medical device container containing a sterile medical device into a second container, at 302. The first sterile medical device container is transparent to RF signals in a particular frequency range. For example, referring to FIG. 1, the IMD 102 may be inserted into the second container 132 while the IMD 102 is stored in the first sterile medical device container 130.

The method 300 may also include closing the second container such that the closed second container fully encloses the first sterile medical device container and the sterile medical device to shield the sterile medical device from an interrogation RF signal, transmitted from an interrogator in the particular frequency range, via RF shielding material affixed to the second container, at 304. In a particular embodiment, the RF shield material is substantially opaque to the RF signals in the particular frequency range. For example, referring to FIG. 2, after the IMD 102 is inserted into the second container 132 while the IMD 102 is stored in the first sterile medical device container 130, each side flap may be folded towards the inside surface of the second container 132 to fully enclose IMD 102 and the first sterile medical device container 130 and to shield the IMD 102 from the RF signals. The method 300 may be performed by a packaging system. The packaging system may be programmed to carry out the method 300 via processor executable instructions stored in a non-transitory computer readable storage medium.

Although the description above contains many specificities, these specificities are utilized to illustrate some of the exemplary embodiments of this disclosure and should not be construed as limiting the scope of the disclosure. The scope of this disclosure should be determined by the claims, their legal equivalents and the fact that it fully encompasses other embodiments which may become apparent to those skilled in the art. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments that implement the systems and methods of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system.

As noted above, embodiments within the scope of the present disclosure include program products comprising machine-readable media for carrying or having machine-executable instructions or data structures stored thereon. Such machine-readable media can be any available media which can be accessed by a general purpose or special purpose computer or other machine with a processor. By way of example, such machine-readable media can comprise RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing descriptions of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A system comprising:
    a first sterile medical device container having a plurality of compartments, wherein the first sterile medical device container is transparent to radiofrequency signals in a particular frequency range;
    a sterile medical device within the first sterile medical device container, wherein the sterile medical device is capable of radiofrequency communication through the first sterile medical device container using the particular frequency range; and
    a second container fully enclosing the first sterile medical device container and the sterile medical device, the second container comprising a first nonconductive layer, a second nonconductive layer, and radiofrequency shielding material that is substantially opaque to the radiofrequency signals in the particular frequency range, the radiofrequency shielding material disposed between the first nonconductive layer and the second nonconductive layer;
    wherein the sterile medical device is disposed within a first compartment of the plurality of compartments, and wherein a tool associated with a procedure for implanting the sterile medical device is disposed within a second compartment of the plurality of compartments.

2. The system of claim 1, wherein the sterile medical device is an implantable medical device.

3. The system of claim 1, wherein the sterile medical device includes a communication device.

4. The system of claim 1, wherein the sterile medical device is configured to:
    power on in response to receiving, from an interrogator, a radiofrequency interrogation signal included in the radiofrequency signals in the particular frequency range.

5. The system of claim 4, wherein the sterile medical device is further configured to transmit a device identification to the interrogator in response to receiving the radiofrequency interrogation signal.

6. The system of claim 5, wherein the sterile medical device does not receive the radiofrequency interrogation signal when fully enclosed by the second container, wherein after the second container is opened, the sterile medical device is able to receive the radiofrequency interrogation signal within the first sterile medical device container.

7. The system of claim 6, wherein the interrogator is located in a sterile environment and the second container is located in a non-sterile environment.

8. The system of claim 1, wherein the radiofrequency shielding material includes an electrically conductive material.

9. The system of claim 8, wherein the radiofrequency shielding material includes a metallic foil.

10. The system of claim 1, wherein at least one of the first nonconductive layer or the second nonconductive layer is made from a plant based material.

11. The system of claim 1, wherein the radiofrequency shielding material is substantially opaque to a particular radiofrequency signal transmitted at 2.45 gigahertz.

12. The system of claim 1, wherein each of the first nonconductive layer, the second nonconductive layer, and the radiofrequency shielding material fully enclose the first sterile medical device container and the sterile medical device.

13. A system comprising:
    a first sterile medical device container having a plurality of compartments,
        wherein the first sterile medical device container is transparent to radiofrequency signals in a particular frequency range;
    a sterile medical device within the first sterile medical device container, wherein the sterile medical device is capable of radiofrequency communication through the first sterile medical device container using the particular frequency range; and
    a second container fully enclosing the first sterile medical device container and the sterile medical device, the second container comprising a first nonconductive layer, a second nonconductive layer, and radiofrequency shielding material disposed between the first nonconductive layer and the second nonconductive layer, wherein the second container is configured to block radiofrequency signals in the particular frequency range from being received at the sterile medical device via the radiofrequency shielding material;
wherein the sterile medical device is disposed within a first compartment of the plurality of compartments, and wherein a tool associated with a procedure for implanting the sterile medical device is disposed within a second compartment of the plurality of compartments.

14. The system of claim 13, wherein the sterile medical device includes an implantable vagus nerve stimulation device.

15. The system of claim 13, wherein the sterile medical device includes a communication device.

16. The system of claim 13, the radiofrequency shielding material is substantially opaque to a particular RF signal transmitted at 2.45 gigahertz.

17. The system of claim 13, wherein at least one of the first nonconductive layer or the second nonconductive layer is made from polymer material.

* * * * *